United States Patent [19]

Field

[11] Patent Number: 5,067,346

[45] Date of Patent: Nov. 26, 1991

[54] PENETRATING MEASURING INSTRUMENT

[75] Inventor: John S. Field, Berowa Heights, Australia

[73] Assignee: Commonwealth Scientific and Industrial Research Organization, Campbell, Australia

[21] Appl. No.: 299,835

[22] PCT Filed: Jul. 7, 1987

[86] PCT No.: PCT/AU87/00202

§ 371 Date: Jan. 10, 1989

§ 102(e) Date: Jan. 10, 1989

[87] PCT Pub. No.: WO88/00691

PCT Pub. Date: Jan. 28, 1988

[30] Foreign Application Priority Data

Jul. 10, 1986 [AU] Australia .................. PH6842

[51] Int. Cl.$^5$ .................................. G01N 3/42
[52] U.S. Cl. ........................................... 73/81
[58] Field of Search ................................. 73/81

[56] References Cited

U.S. PATENT DOCUMENTS

| | | | |
|---|---|---|---|
| 3,077,771 | 2/1963 | Ernst ........................ | 73/81 |
| 4,159,640 | 7/1979 | Lévêque et al. ............ | 73/81 |
| 4,621,523 | 11/1986 | Shabel et al. .............. | 73/81 |

FOREIGN PATENT DOCUMENTS

| | | | |
|---|---|---|---|
| 603531 | 10/1934 | Fed. Rep. of Germany ........ | 73/81 |
| 1129729 | 5/1962 | Fed. Rep. of Germany ........ | 73/81 |
| 184949 | 11/1982 | Japan . | |
| 193047 | 8/1986 | Japan . | |
| 373581 | 6/1973 | U.S.S.R. . | |
| 386316 | 9/1973 | U.S.S.R. .................... | 73/81 |
| 643779 | 1/1979 | U.S.S.R. .................... | 73/81 |
| 1147950A | 7/1983 | U.S.S.R. . | |
| 1040382 | 9/1983 | U.S.S.R. .................... | 73/81 |
| 738606 | 10/1955 | United Kingdom .............. | 73/81 |
| 1399947 | 7/1975 | United Kingdom .............. | 73/81 |
| 1566492 | 4/1980 | United Kingdom . | |

OTHER PUBLICATIONS

Derwent Abstract Accession No. 85-248313/40, 1147950, Kulapov et al, Mar. 30, 1985.
Patent Abstracts of Japan, P174, vol. 7, No. 32, pub. Feb. 8, 1983; JP, A, 57-184949.
Patent Abstracts of Japan, P537, vol. 11, No. 19, Jan. 20, 1987; JP, A, 61-193047.
Derwent Abstract Accession No. H 6087A/39, S79561, Novoselov, Nov. 28, 1977.
Derwent Abstract Accession No. J 2946B/39, G38873, Andreev et al, Dec. 25, 1978.
Gane et al, "The Micro-hardness of Metals ... ", Philosophical Mag. vol. 22, No. 179, Nov. 1970, pp. 881, 883, 885, 888, 890-891 (incomplete).

(List continued on next page.)

Primary Examiner—Tom Noland
Attorney, Agent, or Firm—Nixon & Vanderhye

[57] ABSTRACT

A penetration measuring apparatus comprising a stage for mounting a sample of the material to be tested thereon, a probe having one end thereof proximal to the stage and having a longitudinal axis extending orthogonally of the stage, an ultra-microhardness indenter located in the one end of the probe, and a carriage assembly to which the probe is connected via an intermediate member, a first elastic connector of known stiffness connecting the probe to the intermediate member and a second elastic connector of known stiffness connecting the intermediate member to the carriage. The first and second connectors allow axial movement of the probe but prevent movement of the probe in any other direction. A driving device is provided for driving the carriage towards and away from the stage and a first measuring device measures the movement of the probe relative to a stationary datum. A second measuring device is provided which measures the deformation of the elastic connector connecting the probe to the carriage.

10 Claims, 5 Drawing Sheets

OTHER PUBLICATIONS

Wierenga et al, "Ultramicrohardness Experiments on . . . ", paper presented at Intl Con. on Metallurgical Coatings, San Diego, Calif., U.S.A., Apr. 9–13, 1984, pp. 375–380.

Doerner et al, "A Method for Interpreting the Data from Depth-sensing . . . ", J. Mater. Res., vol. 1, No. 4, Jul./Aug. 1986, pp. 601–609.

Gasilin et al, "Crohardness Tester Recording . . . ", Zavodskaya Lab., vol. 44, No. 3, pp. 364–367, Mar. 1978 (reprinted translation of) contains abst. page and pr. 432.

Gane, "The Direct Measurement of the Strength . . . ", Proc. Roy. Soc. Lond. A. 317, (1970); pp. 367, 369, 371, 373, 376, 378, 380, 382, 384, 386, 388, 390, plate 2.

Shorshorov et al, "Work of Plastic and Elastic Deformation . . . ", Sov. Phys. Doki 26(8) Aug. 1981, pp. 769–771.

Loubet et al, "Vickers Indentation Curves of . . . ", MicroInd. Techniques in Materials Science, pp. 72–87, pub. by May 1989.

Jönsson et al, "Hardness Measurements of Thin Films", Solid Films 114 (1984), pp. 257, 259–266, 268, 269.

Nishibori et al, "Ultra-Microhardness of Vacuum . . . ", The Ind Films, 48 (1978), pp. 325–331.

Pethica et al, "Hardness Measurement at Penetration . . . ", Philosophical Mag. A, 1983, vol. 48, No. 4, 593–604, 606.

Bangert et al, "Ultramicrohardness Tester for Use . . . ", Colloid and Polymer Science, vol. 259, pp. 238–240 (1981).

Newey et al, "The Ultra-Microhardness of Ion-Implanted . . . ", Dept. of Physics, Univ. of Lancaster, UK Abstract, pp. 157–166; pub. by May 1989.

Newey et al, "An Ultra-low-load Penetration Hardness . . . ", Phys. F. Sci. Instrum., vol. 15, 1982 UK, pp. 119–122; by May 1989.

Pethica, "Microhardness Tests with Penetration . . . ", Abstract, Brown Boveri Res. Center, 5405 Baden, Switzerland, pp. 147–156; pub. by May 1989.

Ultramicrohardness Tester, UMHT-3; 6 pages; by May 1989.

Nanoindenter Schematic, NANO Microscience; 13 pages; by May 1989.

Micro-Duromat 4000, Reichert-Jung; 5 pages; by May 1989.

Caw, "The Elastic Behaviour of a Sharp . . . ", Jour. of Scientific Ins. (Jour. of Physics E) 1969 Series 2, vol. 2, pp. 73–78.

Loubet et al, "Vickers Indentation . . . ", ASTM Special Tech. Publ 889, Intl Metallographic Society, pp. 73–88, material presented Intl. Metallography Soc. Symposium, Philadelphia, Jul. 1984.

Tabor, "The Hardness of Metals", Oxford Clarendon Press 1951, p. 44.

Johnson, "Contact Mechanics", Cambridge Univ. Press, p. 24, pub. by 1-1991.

Sneddon, "Boussinesq's Problem . . . ", Proc. Conf. Phil. Soc. 1948.44, pp. 492–507.

PENETRATING MEASURING INSTRUMENT

The present invention relates to a penetration measuring instrument for use in ultra-microindentation.

BACKGROUND OF THE INVENTION

The use of penetration devices to obtain information relating to the mechanical characteristics of a material being tested is very well known. Typically, an indenter is forced into a sample of a material and then extracted therefrom, leaving an indentation in the surface of the sample. The depth of penetration, surface or projected area of the indentation and the force applied to the indenter provide information indicative of material properties such as hardness or modulus of elasticity.

The modification of surface layers and the use of surface coatings to provide improved chemical, mechanical, electrical or decorative properties is rapidly increasing. Such modifications include very thin surface treatments such as vacuum deposited coatings, ion-implanted surface layers and surface hardening. In order that the properties of such coatings and layers be better understood, testing apparatus has been developed to carry out ultra-microhardness testing.

Ultra-microindentation is a technique for obtaining information about the mechanical properties of a surface material from relationships between the depth of penetration of an indenter and resistance to its penetration. Ultra-microindentations are produced by pressing the indenter, which is usually a diamond pyramid, into the surface under the control of an ultra-microindenting system (UMIS).

To ensure that the probe of a UMIS does not cause cracking in the sample coating or surface layer and also to ensure that the characteristics of the coating are tested independently of the substrate characteristics, it has been recommended that the depth of penetration should be small in relation to the total layer or coating thickness. As, for example, the depth of penetration of implanted ions typically does not exceed 1 $\mu$m, it is desirable to be able to carry out microhardness testing using penetrations as little as 0.1 $\mu$m. If an indenter with Vickers type geometry is used to produce an indentation of 0.1 $\mu$m depth, the diagonal width of the indentation will be of the order of 0.7 $\mu$m.

Measurement of impressions having widths less than about 1 $\mu$m are impossible to perform without the aid of an electron microscope. Skilled addressees will be aware that electron microscopes are extremely expensive, both in initial purchase cost and operating cost. Consequently, there is a need for a penetration measuring instrument capable of use in ultra-microhardness testing which can provide data indicative of the depth of indentation without the need to perform further measurement. As an indenter will be of known geometry the width surface or projected area of an indenter can be defined if the depth of indentation is known. It has been shown that if a device can provide information indicative of the indenter position and the indenting force at intervals during the loading and unloading phases, the data thus generated is sufficient to allow deductions to be made about the dynamic and static resistance to abrasion, to local penetration and about the static and dynamic elastic properties of the new surface material. That is, it is possible to carry out the appropriate calculations of material properties without recourse to measurement by a microscope of any kind, be it optical, electron or otherwise.

In order for such a penetration measuring apparatus to be successful, the indenter motion should be produced by an actuator which is capable of producing smooth, vibration free motion at very low speed. The effects of any inertial forces which, for example, can arise from dead weight loading, must be avoided as far as possible. In the present invention the solution is to support the indenter by elastic coupling means on a carriage assembly and, as the carriage assembly is moved an indenting force is transferred to the probe. In this way the deflection of the elastic coupling means is always just sufficient to balance the instantaneous resistance to penetration and, provided the indenting mechanism has low mass, and moves slowly, inertial forces are minimal.

SUMMARY OF THE INVENTION

In a preferred embodiment of the present invention, the indenter is smoothly brought to rest at a predetermined indenting force by progressively reducing the indenter velocity to zero as the force approaches its preset final value. Feedback control of final indenter position ensures that the indenting force is maintained at the predetermined level regardless of creep. This system allows the indentation process to proceed smoothly to a preset maximum indenting force in one step, to approach this value in a series of steps, to dwell at each step for a predetermined time, to retract the indenter either completely in one movement or stepwise. Furthermore it is possible to record force and depth at each step or, alternatively, while the indenter is moving. With the aid of a digitally controlled co-ordinate stage, it is possible to translate the test surface with the indenter in contact under constant or changing force.

According to the present invention, there is disclosed a penetration measuring apparatus comprising:

a stage for mounting a sample of a material to be tested thereon;

a probe having an end thereof proximal to said stage and having a longitudinal axis extending orthogonally of said stage;

an ultra-microhardness indenter located in said first end of said probe;

a carriage assembly to which said probe is connected by elastic connection means of known stiffness, said carriage assembly and connection means allowing axial movement of said probe but preventing movement of said probe in any other direction;

means to drive said carriage assembly towards and away from said stage;

means to measure the movement of said probe relative to a stationary datum; and means to measure the deformation of said elastic connection means connecting said probe to said carriage.

BRIEF DESCRIPTION OF THE DRAWINGS

The present invention will now be described by way of example with reference to the accompanying drawings, in which.

DETAILED DESCRIPTION OF THE INVENTION

Figure 1:
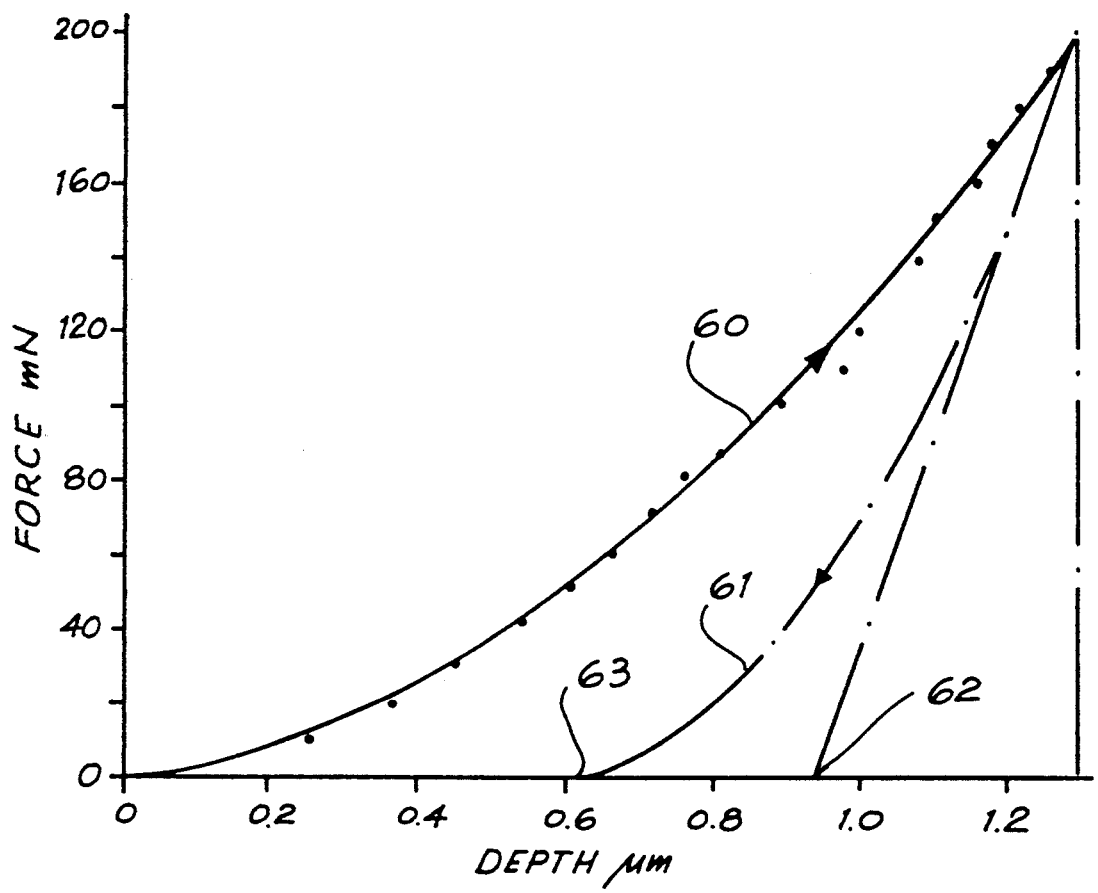
FIG. 1 is a loading/unloading curve for an elastic/plastic material when tested by a device in accordance with the present invention.

Analysis of loading unloading curves may be understood in conjunction with the loading and unloading curves shown in FIG. 1. The loading curve is designated by numeral 60 and the unloading curve by numeral 61.

The surface of the material adjacent to the indentation is assumed to be depressed by an amount similar to that which would be produced by a circular flat frictionless punch with the same cross sectional area as that part of the indentation in contact with the indenter. This deflection is assumed to recover vertically when the indenting force is removed. At least one third of the unloading curve is usually found to be straight and its projection 62 on to the penetration axis represents this recovery.

The final intersection 63 of the unloading curve with the depth axis represents the unrecovered depth of the indentation and the difference between this point and the intersection of the projection of the initial part of the unloading curve represents recovery of the bottom of the indentation. It is therefore possible to separate the total penetration depth into components representing elastic and plastic deformations and to attribute mechanisms to each of them.

Conventional Vickers hardness is determined from the loaded area of contact between the indenter and the indentation which is calculated for the length of the diagonals of a recovered indentation. Since there is little elastic recovery of these diagonals they are also related to depth of penetration and consequently, after removal of contaminants such as the depression of the surface and any deflection of the UMIS structure, loaded area of contact may be calculated from depth. Although the triangular based indenter commonly used in depth measuring systems has no diagonals the same principles apply and contact area can also be calculated from depth of penetration. Hardness values obtained from the UMIS are therefore in principle equivalent to Vickers hardness values and where comparisons are possible have been found to have similar values.

The division of the unloading curve into components due to two different mechanisms allows the contribution to conventional hardness of the permanent plastic deformation and the non-permanent elastic deformation of the material surrounding the indentation to be investigated. The ratio of these two contributions varies for different materials and therefore comparison of hardness values for different materials may be influenced by this ratio, and much investigation remains to be done. One method of discovering the simple hardness and modulus values of a sample using a UMIS, a single force, with any value within a selected range, and a dwell time between the achievement of full force and its removal are specified. The depth of penetration is measured and recorded after the specified dwell. The force is then reduced to a lower value than the specified value and the partially recovered depth is measured and recorded, again after the specified dwell. Ultra-microhardness Hu and elastic modulus E are calculated for these measurements using $$Hu = F/k_1(R_1 - k_2(R_1 - R_2))^2$$

$$E/(1 - \nu^2) = F/(k_3(R_1 - k_2(R_1 - R_2))(R_1 - R_2))$$

in which F is the indenting force, $R_1$ and $R_2$ and the depth measurements, $k_1$ and $k_3$ are constants dependent on the type of indenter used and $k_2$ a constant dependent on the amount by which the force is reduced. Poisson's ratio, can be assumed to be approximately 0.3.

These aspect of hardness are amenable to study with the UMIS and represent one of its applications.

Figure 2:
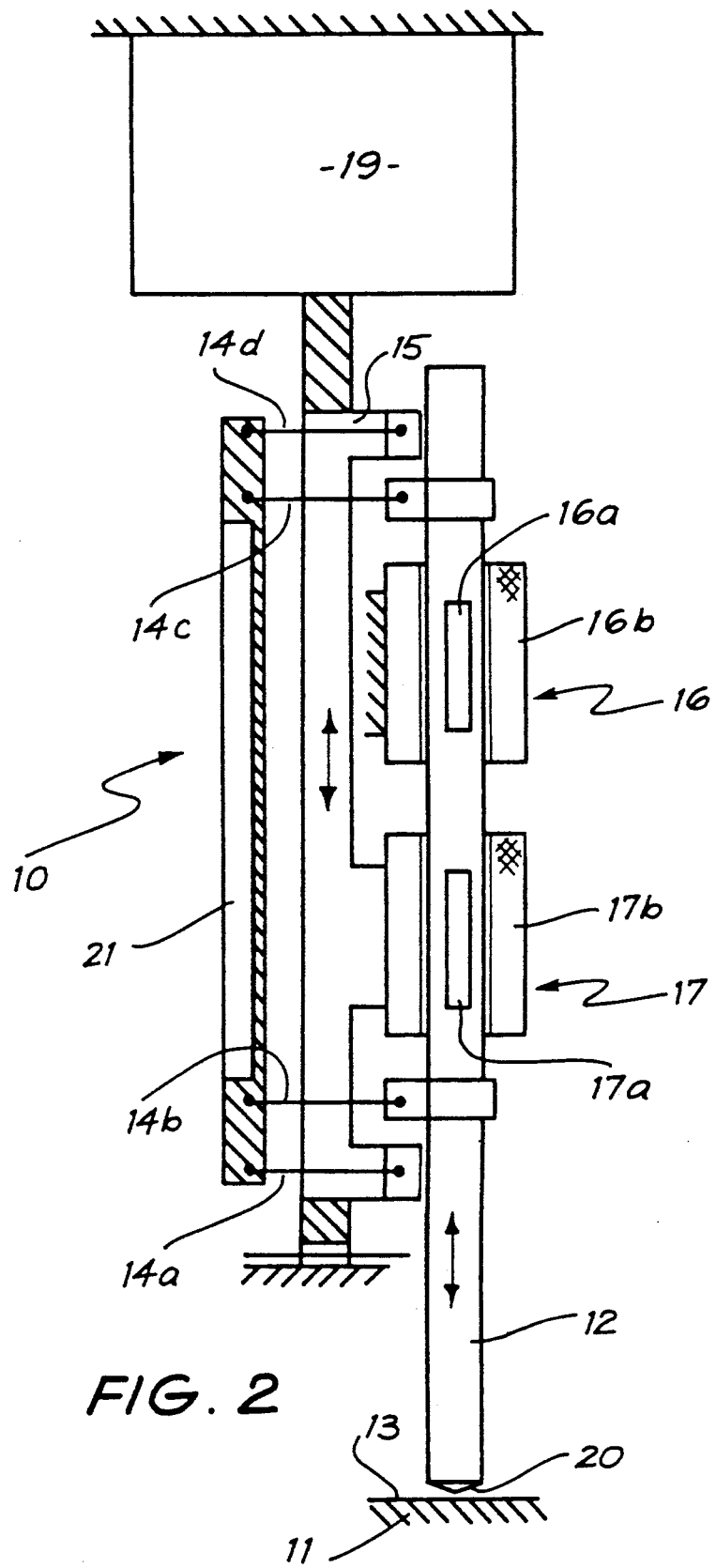
FIG. 2 is a schematic cross-sectional view of a preferred embodiment of the present invention.

FIG. 2 illustrates a penetration measuring device 10, which embodies the present invention. The embodiment 10 comprises a stage 11 for mounting a sample (not shown) thereon, a probe 12 which extends axially in a direction orthogonal to the planar top surface 13 of the stage 11 and which is connected by elastic connection means 14a, 14b, 14c and 14d to a carriage 15 and an acutator 19 to drive the carriage 15 towards the stage 11. Futhermore, there is a first measurement device 16 which measures the movement of the probe 12 with respect to a datum and a second measuring device 17 which measures movement of the probe 12 relative to the carriage 15 and, therefore, any deformation of the elastic connection means 14a, 14b, 14c and 14d. An ultra-microindenter 20 is located on the end of the probe 12 which is proximal to the surface 13 of the stage 11.

In order to minimize the inertial effects referred to above and to allow accurate measurements of the movement of the components of the embodiment of FIG. 2, it is preferable that the actuator 19 be capable of producing smooth, vibration free motion of the probe 12 at low velocity. Many types of drives suitable for this purpose will be known to skilled addressees but the present applicant has found linear electromagnetic actuators and piezoelectric actuators to be preferable, however, electromagnetic shakers also provide adequate performance. Stiffness within the actuator is of importance in order to maximise control over indenting velocity as the resistance to penetration increases. It is noted that piezoelectric actuators are stiff but are also relatively expensive whilst linear electromagnetic actuators are relatively inexpensive and can be stiffened with positional feedback.

In the embodiment illustrated in FIG. 2, the elastic couplings 14a, 14b, 14c and 14d, take the form of leaf-springs. Such leaf-springs have relatively low and determinable stiffness in the indenting direction but have relatively high stiffness in directions transverse to the indenting direction. It will be clear to skilled addressees that in view of the small size of the indentations made by embodiments of the present invention, the probe must be prevented from moving laterally in order for the apparatus to operate properly.

In the embodiment of FIG. 2, vertical deflections in the coupling members 14a and 14d will also result in a relative lateral movement of the probe in a direction illustrated as across the page. This is accounted for in the preferred embodiment by the compensating effect of deflections in the leaf-springs 14c and 14b which, through interaction with an intermediate member 21 and leaf springs 14a and 14d assure that no "across the page" lateral movement of the probe 12 occurs. Leaf springs 14c and 14b are selected such they shorten laterally by precisely the same amount as springs 14a and 14d in response to a given vertical displacement of the probe 12 relative to the carriage 15. In the simplest case this can be achieved by making springs 14a, 14b, 14c and 14d of identical stiffness and length. In the embodiment of FIG. 2, the first and second measuring means 16, 17 take the form of non-contacting displacement measuring devices. There are cores 16a, 17a embedded within the probe 12 which, in this case, must be made from a light, non-magnetic material, such as, for example, titanium aluminium alloy or hyrilium. Magnetic cores 16a, 17a form the moving elements of linear variable differential transformers (L.V.D.T.) however other forms of inductive measuring devices could be used. This arrangement provides virtually infinite resolution of measurements. Alternatively, one or both of the measuring apparatus may take the form of a capacitance measuring device.

It should be noted that because the first measuring means 16 measures the movement of the probe with respect to a datum, it provides an output including information regarding the amount of penetration of the indenter 20 into a sample. As the non moving part 17b of the second measuring device 17 is rigidly fixed to the carriage 15, an output indicating movement of the probe 12 relative to the carriage 15 is provided. Thus, deflection of the springs 14a, 14b, 14c and 14d is measured and the actual load acting on the indenter can be precisely calculated. Furthermore, it should be realised that the arrangement of offsetting the probe 12 with respect to the drive carriage 15 is non-essential. A concentrically arranged embodiment is described hereinafter but the offset arrangement of the embodiment of FIG. 2 has been found to provide ease in calibration.

In use, a sample (not shown) is mounted on the surface 13 of the stage 11 beneath the indenter 20. The actuator drives the carriage 15 downward and, in turn, the probe 12 is also carried downwards. The motion of the probe 12 and the carriage 15 are the same until the indenter 20 contacts the sample surface and the springs 14a, 14b, 14c and 14d deflect. This deflection is identical to the relative movement between the probe 12 and carriage 15 and, it is therefore, precisely measured by the second measuring means 17. Consequently, the instant of contact between the indenter 20 and the sample can be ascertained and the force acting on the probe can be precisely calculated. Any relative movement of the probe 12 measured by the first measuring means 16 after the moment of contact detected by the second measuring means 17 is indicative of penetration by the indenter 20 into the sample.

To derive loading and unloading curves, a maximum force, a force increment, a dwell and a rate of incrementation are specified. The indenter is brought into contact with the surface at the lowest force in the selected range. The indenting force is then incremented to the selected maximum value at the specified rate and then decremented at the same rate. Depth of penetration is recorded at the end of the dwell between each increment or decrement from the point of contact until the force is reduced to zero.

Loading/unloading plots may be constructed and displayed with a best fit line inserted tangent to the initial part of the unloading curve. Hardness values may be calculated for each force level for which the loading-/unloading plots are constructed, on the basis that the tangent to the initial part of the unloading curve is independent of the depth of penetration. Alternative plots of hardness versus the force increment or hardness versus depth of penetration may be displayed.

Using the present invention, it is possible to monitor total indentation, indentation velocity and the load on the indenter simultaneously. Using an appropriate control system, it is also possible to continue driving the actuator 19 after contact until the predetermined test load is almost reached then reduce the indentation speed so that overshooting of the test load value does not occur.

Figure 3:
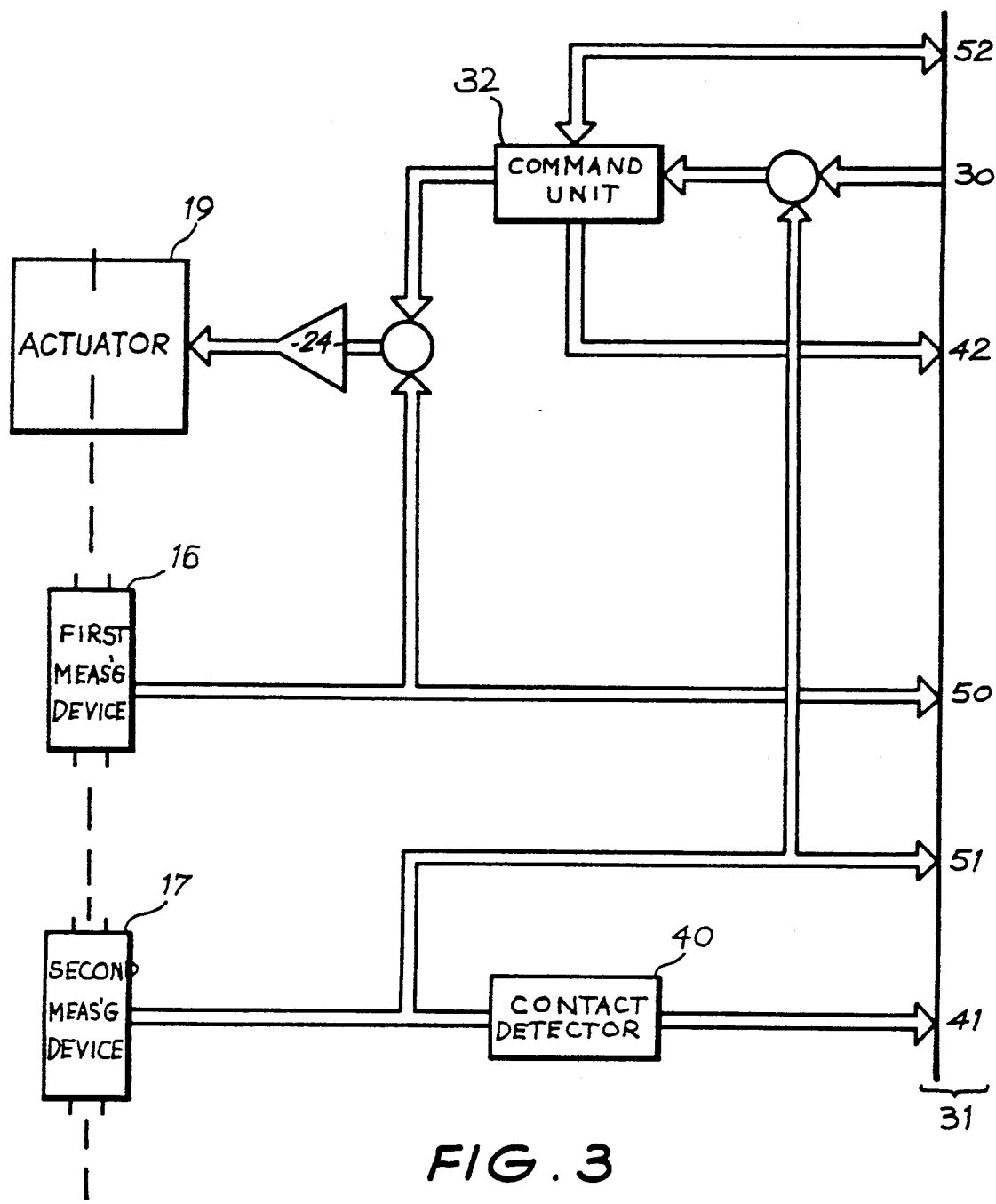
FIG. 3 is a schematic representation of the control system used to operate the present invention.

The control system of the preferred embodiment is illustrated schematically in FIG. 3. A force command signal 30, which is proportional to a desired load and is generated by a computer 31, is relayed to a command unit 32, which takes the form of a linear, analogue ramp generator. The output of the ramp generator is a voltage ramp and the rate of change of the voltage ramp is proportional to the indentation speed. Thus, slope of the ramp is used to control the indentation speed of the actuator 19. In order for the indentation speed to be controlled, information from the first measuring device 16 is continually compared with the ramp slope, an error signal is generated and the current or voltage from the driver 24 to the actuator 19 is varied accordingly. Thus, indenter velocity and displacement can be accurately controlled even though the probe 12 and the carriage 15 of FIG. 2 are not rigidly fixed together.

The output of the second measuring means 17 is compared with the force command signal 30; an error signal is generated to vary the slope of the command ramp as the measured force approaches the same value as the force command signal 30. The slop of the ramp may be reduced to zero when the measured load signal is the same as the command load signal or reversed when the measured load signal exceeds the force command signal.

Furthermore, contact detector 40 generates contact signal 41 in response to the generation of a positive force by the second measuring device 17 and the command unit 37 generates a full force signal 42 when the measured force signal is the same value as the force command signal. The position signal 50 and force signal 51 are continuously recorded by the computer 31 and control lines 52 exist between the computer 31 and the command unit 37 to allow initialisation of the system.

Figure 4:
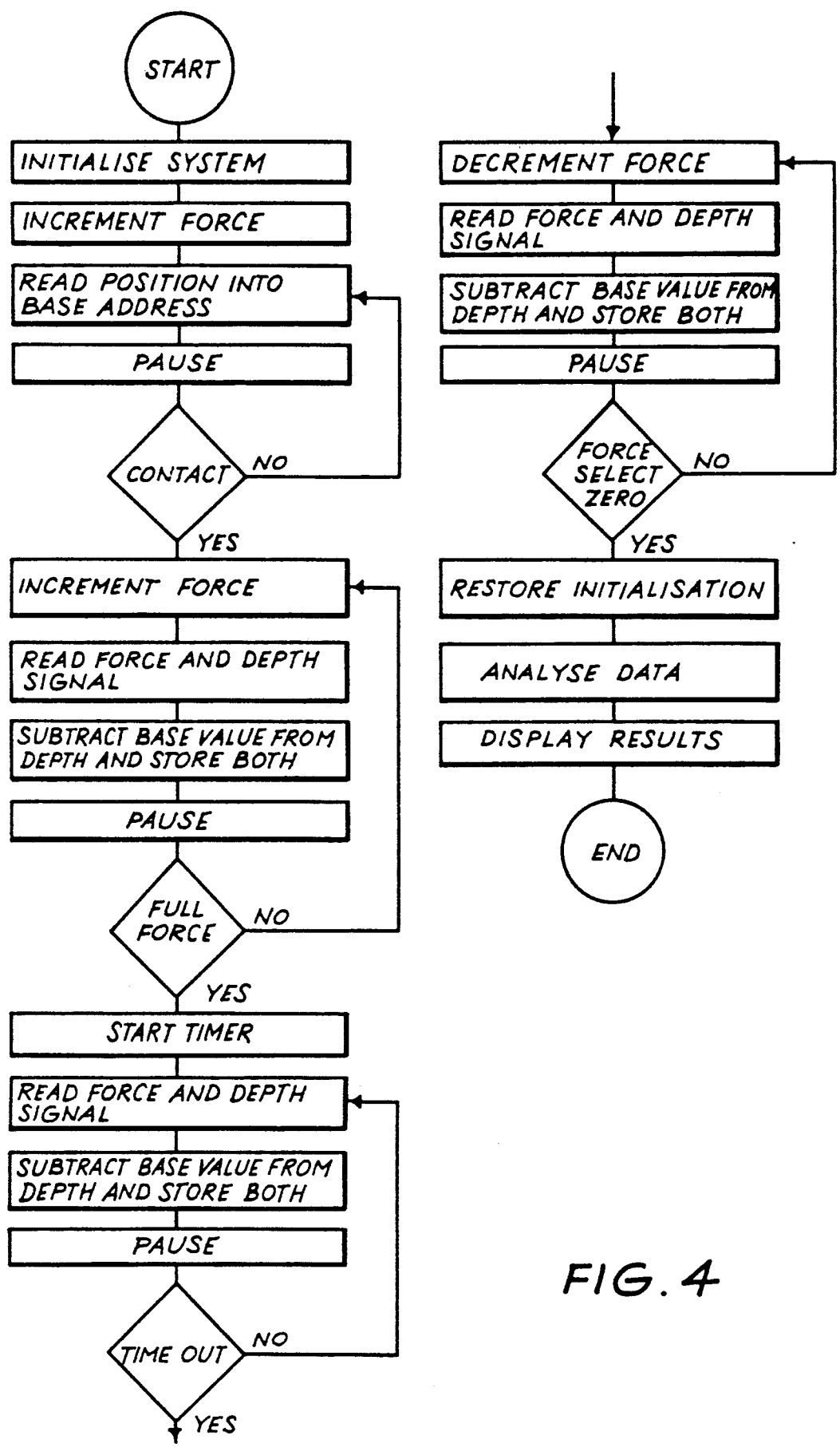
FIG. 4 is a control system flow chart.

A suitable computer programme is shown in skeleton form in the flow chart of FIG. 4. It comprises a series of loops controlling the four main phases of the indentation process and is considered to be self-explanatory.

Figure 5:
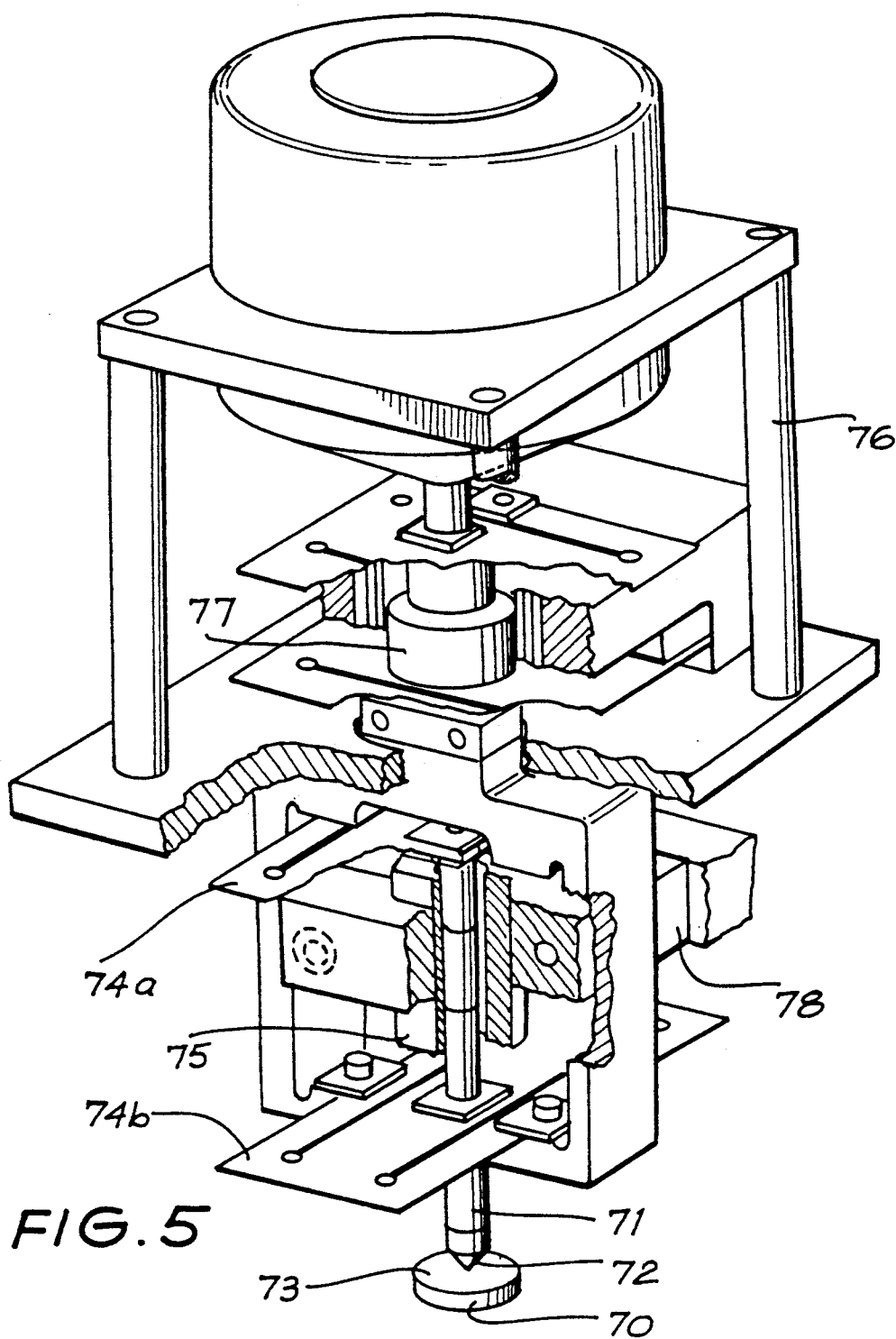
FIG. 5 is a further embodiment of the present invention.

Finally, a second embodiment of the present invention is illustrated in FIG. 5. This embodiment comprises stage 70 for mounting a sample thereon and a probe 71 with a micro-indenter 72 in the lower end thereof extending axially in a direction orthogonal to the planar upper surface 73 of the stage 70. The probe 71 is connected by elastic coupling means in the form of spring plate 74a, 74b to a carriage 75. The carriage 75 is in turn connected to a housing 80 by plate springs 76a, 76b. Plate springs 76a, 76b are slit at right angles to the slits in plate springs 74a, 74b, thus ensuring axial movement of the probe 71. In this embodiment, a first measuring device comprising a concentric capacitor 77 is used to measure the movement of the carriage relative to a datum and a second measuring device 78 comprising an L.V.D.T. or other inductive measuring device is used to measure movement of the probe 71 relative to the same datum. Thus, the deformation of the elastic connection means is also measured, being the difference between the measurements of the first and second measuring devices 77 and 78.

Also it is possible to perform a scratch test using the present invention. A force value, a length of traverse, a traverse rate and a number readings may be specified. The indenter is brought into contact with the surface at the specified force which is maintained while the specimen is traversed through the specified distance at the specified rate. The depth of penetration is measured at the specified number of intervals and recorded. The embodiment of FIG. 2 is capable of applying forces in 3 ranges:

From the foregoing it will be clear to a skilled addressee that apparatus may take many forms without departing from the scope or spirit of the present invention.

I claim:

1. A penetration measuring apparatus comprising:
   a stage for mounting a sample of the material to be tested thereon;
   a probe having one end thereof proximal to said stage and having a longitudinal axis extending orthogonally of said stage;
   an ultra-micro hardness indenter located in said one end of said probe;
   a carriage assembly to which said probe is connected via only an intermediate member, first elastic connection means of known stiffness connecting said probe to said intermediate member and second elastic connection means of known stiffness connecting said intermediate member to said carriage assembly, said first and second elastic connection means thereby allowing axial movement of said probe but preventing movement of said probe in any other direction;
   means for driving said carriage assembly towards and away from said stage;
   first means for measuring the movement of said probe relative to a stationary datum; and
   second means for measuring the deformation of said first and second elastic connection means connecting said probe to said carrier assembly.

2. Apparatus according to claim 1 in which said probe is made from a light non magnetic material.

3. Apparatus according to claim 2 in which at least one of said measuring means is a linear variable differential transformer having a moveable magnetic core embedded in said probe.

4. Apparatus according to claim 1 in which
   said first elastic connection means comprises at least two leaf springs connected to said probe and extending laterally therefrom to said intermediate member which is axially parallel to said probe; and
   said second elastic connection means comprises at least two leaf springs connected to said intermediate member and extending laterally therefrom and connected to said carriage assembly;
   axial movement of said probe causing deflections and corresponding shortening of said leaf springs wherein said shortening is identical for all leaf springs.

5. Apparatus according to claim 4 wherein said leaf springs are all of identical stiffness and length.

6. Apparatus according to claim 1 in which each said elastic connection means comprises at least two spring plates.

7. Apparatus according to claim 1 in which said drive means comprises an electromagnetic actuator.

8. Apparatus according to claim 1 including a control system further comprising a command unit in the form of a ramp generator, the output of said generator being a voltage ramp and the rate of change of said voltage ramp being proportional to indentation speed;
   an actuator driver;
   and a servo system to compare the output of said first measuring means with the output of said command unit, to generate an error signal representative of any difference in said first measuring means output and said command unit output and to vary an input signal to the drive means to maintain the indenter speed indicated by said ramp rate of change.

9. An apparatus according to claim 8 in which said control system further comprises a servo system to compare a force signal generated by the second measuring means with a signal indicative of a test force and to provide a signal to said command unit to generate a ramp of positive gradient when said measured force signal is less than said test force signal, to generate a slope of zero gradient when said measured force signal is equal to said test force signal and to generate a ramp of negative gradient when said measured force signal is greater than said test force signal.

10. Apparatus according to claim 1 in which said drive means comprises a piezo-electric actuator.

* * * * *